United States Patent [19]

Plath et al.

[11] Patent Number: 5,123,955

[45] Date of Patent: * Jun. 23, 1992

[54] PHENYLALKENYLCARBOXYLIC ACIDS AND THEIR ESTERS

[76] Inventors: Peter Plath, 13 Hans-Balcke-Strasse, 6710 Frankenthal; Karl Eicken, 12 Am Huettenwingert, 6706 Wachenheim; Norbert Goetz, 25 Schoefferstrasse, 6520 Worms 1; Jochen Wild, 7 An der Marlach, 6705 Deidesheim; Norbert Meyer, 22 Dossenheimer Weg, 6802 Ladenburg; Bruno Wuerzer, 13 Ruedigerstrasse, 6701 Otterstadt, all of Fed. Rep. of Germany

[*] Notice: The portion of the term of this patent subsequent to Jun. 12, 2007 has been disclaimed.

[21] Appl. No.: 424,990

[22] Filed: Oct. 23, 1989

Related U.S. Application Data

[62] Division of Ser. No. 217,563, Jul. 11, 1988, Pat. No. 4,933,001.

[30] Foreign Application Priority Data

Jul. 23, 1987 [DE] Fed. Rep. of Germany ....... 3724399

[51] Int. Cl.$^5$ .................... C07D 209/48; A01N 37/32
[52] U.S. Cl. .......................................... 71/95; 71/74; 548/513
[58] Field of Search ................. 548/513; 71/74, 95

[56] References Cited

U.S. PATENT DOCUMENTS

| | | | |
|---|---|---|---|
| 4,292,070 | 9/1981 | Wakabayashi | 548/513 |
| 4,420,327 | 12/1983 | Jikihara | 548/513 |
| 4,439,229 | 3/1984 | Swithenbank | 548/513 |
| 4,670,042 | 2/1987 | Haga | 548/513 |
| 4,844,733 | 7/1989 | Eiken | 548/513 |

FOREIGN PATENT DOCUMENTS 59-155358 9/1984 Japan ................................. 548/513

OTHER PUBLICATIONS

Matsumoto, Chem Abs 105, 60524v (1986).
Plath, Chem Abs 107, 198078a.

Primary Examiner—Mark L. Berch

[57] ABSTRACT

Phenylalkenylcarboxylic acid and esters thereof of the general formula I

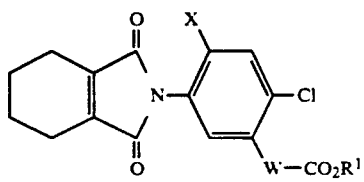

where X is hydrogen or fluorine, $R^1$ is hydrogen, $C_1$-$C_6$-alkyl, $C_5$- or $C_6$-cycloalkyl, ($C_1$-$C_4$-alkoxy)-$C_2$-$C_4$-alkyl or ($C_1$-$C_4$-alkylthio)-$C_2$-$C_4$-alkyl; W is a divalent radical —CH=$CR^2$—; —CH=CY—; —CH=$CR^2$—$CH_2$—; —CH=$CR^2$—CH=$CR^3$— or

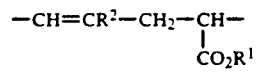

where Y is chlorine or bromine and $R^2$ and $R^3$ are each hydrogen or $C_1$-$C_4$-alkyl, with the proviso that X is not F when W is —CH=$CR^2$—, their manufacture, and their use as herbicides.

3 Claims, No Drawings

PHENYLALKENYLCARBOXYLIC ACIDS AND THEIR ESTERS

This application is a division of application Ser. No. 217,563, filed on Jul. 11, 1988, now U.S. Pat. No. 4,933,001.

The present invention relates to phenylalkenylcarboxylic acids which are substituted in the 5-position by tetrahydro-2H-isoindole-1,3-dione (tetrahydrophthalimide) and their esters, a process for their preparation and their use as herbicides.

It is known that certain isoindoledione-substituted cinnamates can be used as herbicides. These compounds, which are disclosed in Japanese Preliminary Published Application 59/115 358, are of the general formula Z

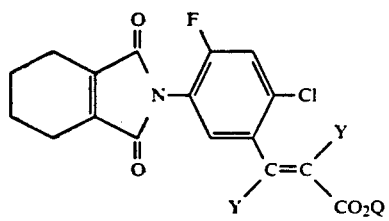

where Y is hydrogen or methyl and Q is alkyl, in particular ethyl. Furthermore, European Laid-Open Application 68,822 discloses the structure $Z^1$:

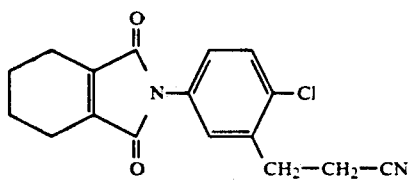

However, their herbicidal action and their toleration by crops are in no way satisfactory in practice.

It is an object of the present invention to provide herbicides which are better tolerated and at the same time more effective against weeds.

We have found that this object is achieved by the novel compounds of the general formula I

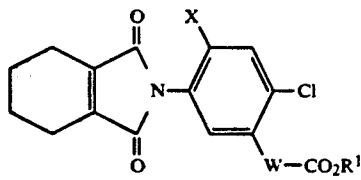

where X is hydrogen or fluorine, $R^1$ is hydrogen, $C_1$-$C_6$-alkyl, $C_5$- or $C_6$-cycloalkyl, ($C_1$-$C_4$-alkoxy)-$C_2$-$C_4$-alkyl or ($C_1$-$C_4$-alkylthio)-$C_2$-$C_4$-alkyl, W is a divalent radical —CH=$CR^2$—, —CH=CY—, —CH=$CR^2$—$CH_2$—, —CH=$CR^2$—CH=$CR^3$— or

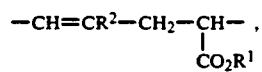

where Y is chlorine or bromine and $R^2$ and $R^3$ are each hydrogen or $C_1$-$C_4$-alkyl, with the proviso that X is not F when W is —CH=$CR^2$—.

The novel substances (I) are very suitable, for example, for controlling weeds in wheat, corn, rice and soybean.

The substances of the formula I are obtained, for example, by reacting an aniline of the formula II with the anhydride III in a suitable solvent at from 40° to 120° C. in the course of, in general, not more than 24 hours (scheme A):

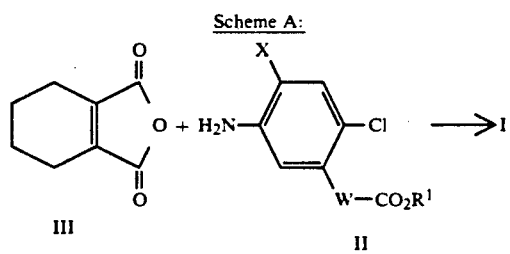

The reaction is advantageously carried out in a suitable solvent, such as an aliphatic hydrocarbon (e.g. hexane or naphtha), an aromatic hydrocarbon (e.g. toluene or xylene), an ether (e.g. tetrahydrofuran or diethylene glycyol dimethyl ether), a lower fatty acid (e.g. acetic acid or propionic acid) or a mixture of the latter with water. The reaction product is isolated in a conventional manner by extraction, precipitation and, if necessary, subsequent recrystallization and, if required, is purified by chromatography.

The anhydride III is a known intermediate. Anilines of the formula II are obtained by subjecting an appropriate nitro compound to catalytic hydrogenation or to reduction with a suitable reducing agent (e.g. iron in methanol/glacial acetic acid) to give II (scheme B):

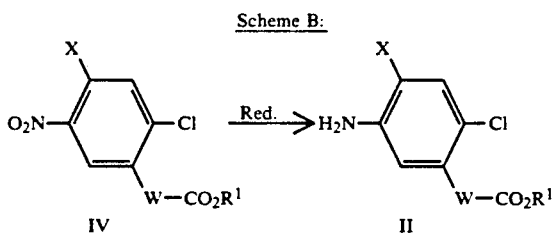

The nitro compounds IV, which are likewise novel, can be obtained in a known manner, and it is possible to use various methods depending on the nature of the radical W:

1. If W is —CH=$CR^2$—, the nitro compound (2) is obtained, for example by nitration of the known α-alkylcinnamate (1) according to scheme (1):

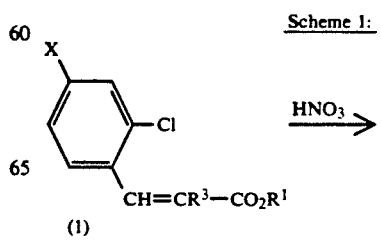

-continued

Scheme 1:

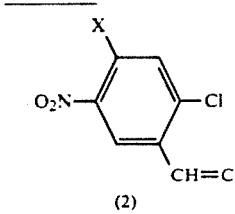

(2)

Where X is H, the nitration is advantageously carried out with 96–100% strength nitric acid at from −10° to 0° C. The corresponding fluorine compound can also be nitrated in concentrated sulfuric acid as a diluent.

The parent ester (1) is obtained in a conventional manner by esterifying the acid (5), which is prepared from benzaldehyde (3) by reaction with malonic acid or a carboxylic anhydride (4) (scheme 2):

Scheme 2:

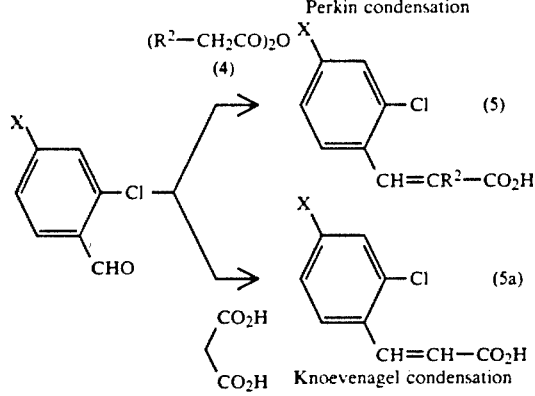

The conditions which are suitable for the preparation of (5) and (5a) are known; the Perkin condensation is described by, for example, Johnson, Org. Reactions 1 (1942), 210 et seq.; a synoptic report of the Knoevenagel condensation appears in Org. Reactions 15 (1967), 204.

A special case is encountered when, in (2), both X and $R^1$ are hydrogen:

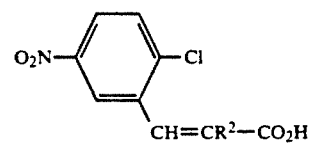

(2a)

The 2-chloro-5-nitrocinnamic acid (2a) is obtained directly from the nitrobenzaldehyde (6) and the anhydride (4) (scheme 3):

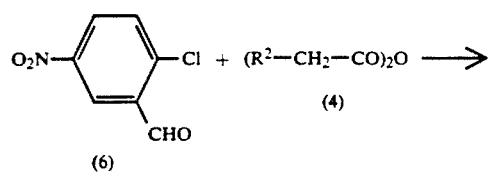

-continued

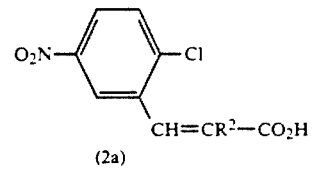

(2a)

The analogous reaction of (6) with malonic acid gives the cinnamic acid (2b) which is unsubstituted in the α-position:

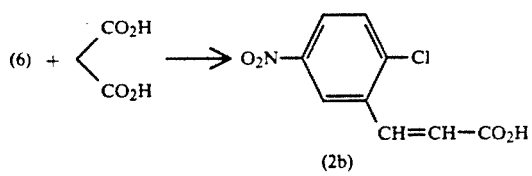

(2b)

The corresponding cinnamates 2c and 2d are obtained by esterification of 2a and 2b.

2. If W is the (halogenated) radical —CH═CY—, the required nitro compound (8) is prepared either by halogenation of the ester (1a) ($\triangleq$ 1 where $R^2$ is H) and subsequent dehydrohalogenation followed by nitration (scheme 4), or by halogenation and dehydrohalogenation of a nitrocinnamate (2d), as shown in scheme 5:

Scheme 4:

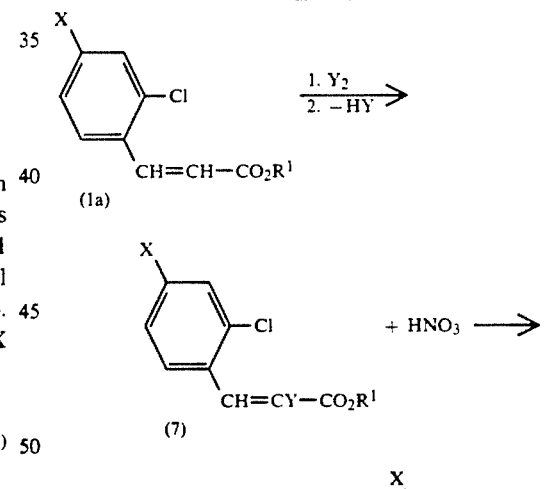

Scheme 5:

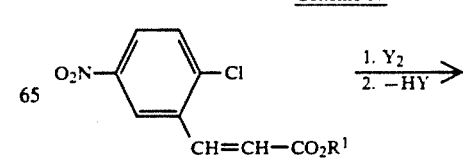

-continued
Scheme 5:

The preferred method for the preparation of a compound Ib where W is —CH=CY—CO$_2$R$^1$ is, however, via halogenation and dehydrohalogenation of the structure Ia (scheme 6):

Scheme 6:

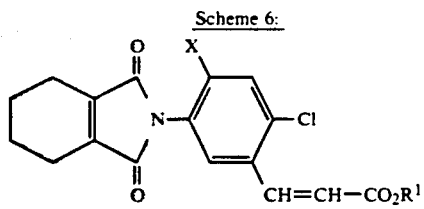

While bromine readily undergoes an addition reaction with Ia (Y=Br), an addition reaction with chlorine requires the measures described in the Examples.

The bases required for dehydrohalogenation are, for example, triethylamine, pyridine or α-picoline.

The solvent preferably used in the addition reaction with halogen is 1,1,1-trichloroethane or glacial acetic acid, while the dehydrohalogenation is carried out in methylene chloride, ethyl acetate, 1,1,1-trichloroethane or the like.

3. If W contains a chain of more than two carbon atoms, the process for the preparation of the required nitro compound depends on whether X is fluorine or hydrogen:

3.1 If X is hydrogen, a nitrocinnamaldehyde (9) or the nitrobenzaldehyde (6) is used as the starting material. The required carbon chain W is then obtained by reacting (9) either with malonic acid in pyridine or with the oxazoline (10) in toluene or subjecting (9) to a Perkin condensation with the anhydride (4).

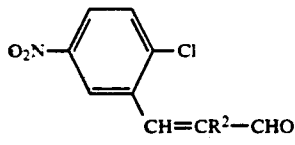
(9)

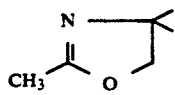
(10)

Alternatively, the carbon chain W can be obtained by reacting (6) with the phosphonate (11) or (9) with the phosphonate (12) in the presence of sodium hydride in dioxane or dimethylformamide (Horner-Emmons reaction).

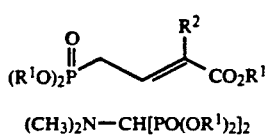
(11)

(CH$_3$)$_2$N—CH[PO(OR$^1$)$_2$]$_2$   (12)

(12) is prepared according to Angew. Chem. 80 (1968, 364.

3.2 If, on the other hand, X is fluorine, the carbon chain is first synthesized by Knoevenagel condensation or a Horner-Emmons reaction from the benzaldehyde (13) or the cinnamaldehyde (14)

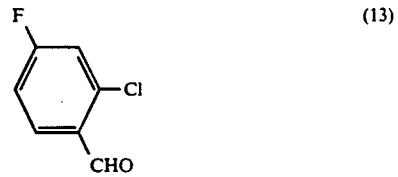
(13)

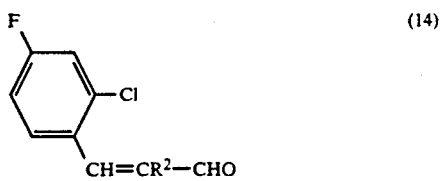
(14)

and the nitro group is then introduced.

The Examples described provide more details on the synthesis of a chain of more than 2 carbon atoms.

4. Finally, if W is

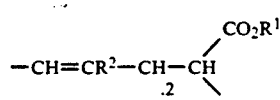

the required aniline derivative IIIa can be obtained by reacting an appropriate nitrocinnamylidene malonate with NaBH$_4$ in the presence of copper (II) acetate.

A typical example of the preparation of a compound I is the following:

EXAMPLE 1

Desired compound

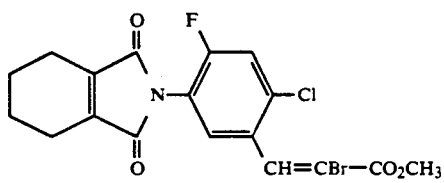

1.1. Methyl 2-chloro-4-fluoro-5-N-(3,4,5,6-tetrahydrophthalimido)-cinnamate was first prepared similarly to the process described in Japanese Preliminary Published Application 59/115 358.

1.2. 5 g of bromine, dissolved in 20 ml of CH$_2$Cl$_2$, are added dropwise to a solution of 10 g of methyl cinnamate in 100 ml of CH$_2$Cl$_2$, and the mixture is then heated at the boil for a further hour. It is allowed to cool to 25° C., 8 ml of triethylamine are added and stirring is carried out for 14 hours at 25° C. The mixture is extracted twice with 50 ml of water, dried and evaporated down. The residue is dissolved in toluene and the solution is chromatographed over silica gel. After the toluene has been stripped off, a solid (mp. 121°–123° C.; yield 9.5 g, i.e. 78%; active ingredient No. 1-1in Table 1) remains. The other compounds in this Table were obtained by appropriate modification from other starting materials.

EXAMPLE 2

Desired compound: active ingredient 2-2 in Table 2.

2.1. 4-(2-Chloro-5-nitrophenyl)-3-methyl-3-butenoic acid A solution of 6.6 g of tetraethyl dimethylaminomethyllenediphosphonate in 25 ml of dioxane is added dropwise to a suspension of 0.6 g of sodium hydride in 25 ml of absolute dioxane with slight cooling (23°-26° C.) and the mixture is stirred for one hour. Thereafter, a solution of 4.5 g of 3-(2-chloro-5-nitrophenyl)-2-methyl-2-propenal in 25 ml of dioxane is added dropwise and the mixture is then heated at 50° C. for 12 hours. The solvent is then removed in a rotary evaporator, the residue is dissolved in diethyl ether (150 ml) and the solution is extracted twice by shaking with water. Drying and evaporation give 6.8 g (84%) of an oily liquid of the structure:

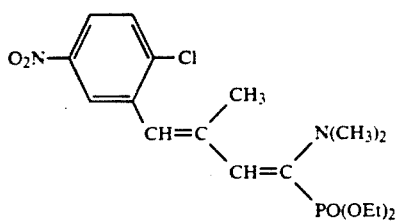

By boiling this enamine for one hour with 200 ml of concentrated HCL, pouring the mixture into 1 L of ice water and extracting with diethyl ether, drying and evaporating down, 4.4 g of liquid are obtained.

2.2. Methyl 4-(2-chloro-5-nitrophenyl)-3-methyl-3-butenoate 4.3 g of the acid obtained according to 2.1 are dissolved in 60 ml of methanol at room temperature and the solution is saturated with HCl gas, the temperature increasing to about 29° C. After the solution has stood for 16 hours, the methanol is distilled off, the residue is dissolved in diethyl ether and the solution is washed with aqueous Na bicarbonate and then with water, dried with MgSO$_4$ and evaporated down, 3.3 g (72%) of the desired ester being obtained.

2.3. Methyl 4-(2-chloro-5-aminophenyl)-3-methyl-3-butenoate A solution of 3.3 g of the nitroarylbutenoate obtained under 2.2 in a mixture of 17 ml of methanol and 17 ml of glacial acetic acid is added dropwise to a suspension of 4.1 g of iron powder in a mixture, heated to 60° C., of 34 ml of methanol and 9 ml of glacial acetic acid. The mixture is heated at the boil for 2 hours and then filtered, the filtrate is evaporated virtually to dryness and the residue is stirred with 150 ml of ethyl acetate. The solution is washed with water, dried and evaporated down to give 3.2 g of an oil.

2.4. 2-{4-Chloro-3-[(2'-methyl-3'-methoxycarbonyl-1'-propenyl)-phenyl]}-4,5,6,7-tetrahydro-2H-isoindole-1,3-dione 3.0 g of the aniline derivative obtained according to 2.2 and 1.9 g of tetrahydrophthalic anhydride are dissolved in 20 ml of glacial acetic acid and the solution is heated at the boil for 2 hours. Thereafter, the solvent is evaporated off, the residue is dissolved in ethyl acetate and the solution is washed with aqueous Na bicarbonate and then with water, dried and evaporated down. The oily residue is chromatographed over silica gel with 95:5 hexane/acetone. Finally, 1.4 g of the product remain as an oil; $n_D^{24} = 1.5579$. (Active ingredient 2-2 in Table 2; other compounds can be prepared in a similar manner).

EXAMPLE 3

Desired compound

2-{4-Chloro-3-[(4'-methoxycarbonyl-1',3'-butadienyl)-phenyl]}-4,5,6,7-tetrahydro-2H-isoindole-1,3-dione (active ingredient 4-1 in Table 4)

3.1. 5-(2'-Chloro-5'-nitrophenyl)-2,4-pentadienoic acid 10.15 g of 2-chloro-5-nitrocinnamaldehyde are added to a solution of 6.05 g of malonic acid in 20 ml of pyridine at 25° C., followed by 0.45 g of piperidine. The mixture is then heated at the boil for 3 hours. After cooling, it is poured into a solution of 20 ml of concentrated HCl in 50 ml of ice water, the product being precipitated. The crude product (11.9 g) is filtered off under suction, washed with water and dried under reduced pressure at 50° C. and then chromatographed in 8:2 toluene/acetone over silica gel, 5.6 g of the desired acid being obtained as a white solid.

3.2. Methyl 5-(2'-chloro-5'-nitrophenyl)-2,4-pentadienoate A solution of 5.4 g of the carboxylic acid obtained according to 3.1 in 60 ml of methanol is saturated with HCl gas and left to stand for 16 hours. The solvent is evaporated off, after which the residue is stirred with NaHCO$_3$/water, filtered off under suction and washed with water. Drying under reduced pressure at 50° C. gives 3.5 g of the ester (mp. 132° C.; 62% of theory).

3.3. Methyl 5-(2'-chloro-5'-aminophenyl)-2,4-pentadienoate 9 ml of glacial acetic acid are poured into a suspension of 4.3 g of iron powder in 35 ml of methanol, which is heated at 60° C., and subsequently a solution of 3.4 g of the ester described under 3.2 in a mixture of 17 ml of methanol and 17 ml of glacial acetic acid is added dropwise. The mixture is refluxed for 1 hour and then evaporated down, the residue is stirred with ethyl acetate and the solution is washed with water, dried and evaporated down to give 2.9 g (96% of theory) of a colorless oil.

3.4. Reaction with 3,4,5,6-tetrahydrophthalic anhydride 2.2 g of tetrahydrophthalic anhydride and 2.9 g of the aniline derivative obtained according to 3.3 are dissolved in 25 ml of glacial acetic acid and the solution is stirred for two hours at 40° C. and then for 2 hours at 110° C. After the solvent has evaporated off, the oily residue is dissolved in hexane and the solution is chromatographed over silica gel. 2.3 g (59% of theory) of a compound of melting point 127°-130° C. are obtained. According to NMR analysis, the product is a mixture of the following stereoisomers:

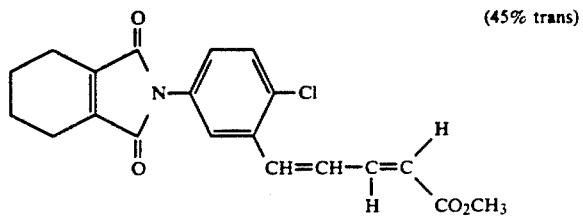

(45% trans)

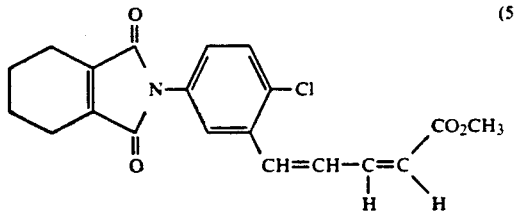

(55% cis)

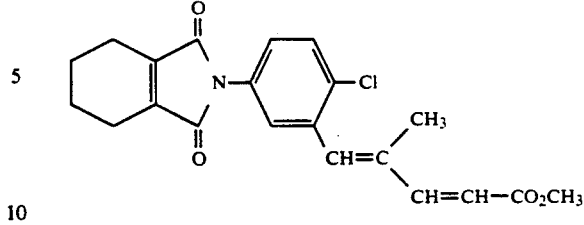

EXAMPLE 4

Desired compound

2-{4-Chloro-3-[(4'-methoxycarbonyl-2'-methyl-1',3'-butadienyl)-phenyl]}-4,5,6,7-tetahydro-2H-isoindole-1,3-dione (active ingredient 4-2 in Table 4)

4.1. 5-(2'-Chloro-5'-nitrophenyl)-4-methyl-2,4-pentadienoic acid 0.3 g of a 40 percent strength NaHSO$_3$ solution is added to a mixture of 9 g of 2-chloro-5-nitro-α-methyl-cinnamaldehyde and 10.4 g of 2,4,4-trimethyloxazoline in 50 ml of toluene, and the mixture is refluxed for 10 hours. It is evaporated down, and 10 ml of water and 10 ml of concentrated HCl are added to the crude product of the structure

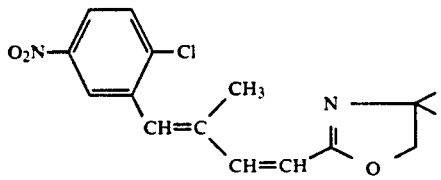

Heating at 100° C. for 7 hours results in cleavage of the oxazoline ring. The crude product is filtered off under suction, washed with water and dried. Yield: 7.1 g (66%), mp. 178°-185° C.

4.2. Methyl 5-(2'-chloro-5'-nitrophenyl)-4-methyl-2,4-penadienoate

The acid obtained according to 4.1 is esterified with methanol/HCl; 49% yield (mp.: 87°-90° C.).

4.3. Methyl 5-(2'-chloro-5'-aminophenyl)-4-methyl-2,4-pentadienoate

The reduction of the nitro compound prepared according to 4.2 is carried out as described under 3.3. 2.9 g (97%; mp.: 47°-50° C.) of the aniline derivative of the following structure:

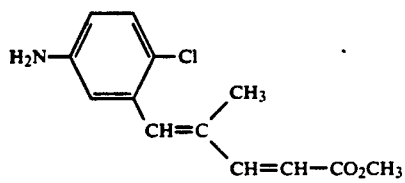

is obtained.

4.4 The aniline derivative is prepared according to 4.3 is reacted with tetrahydrophthalic anhydride in glacial acetic acid in the manner described. The crude product is purified by chromatography over silica gel with 1:1 hexane/acetone and is recrystallized from 80% strength methanol to give 1.5 g (35% of theory) of the active ingredient (mp.: 160°-162° C.) which is listed in Table 4 as compound No. 4-2. The compound is presumably a mixture of stereoisomers.

EXAMPLE 5

Desired compound

2-{4-Chloro-3-[(4'-ethoxycarbonyl-3'-methyl-1',3'-butadienyl)-phenyl]}-4,5,6,7-tetrahydro-2H-isoindole-1,3-dione (active ingredient 4-3 in Table 4)

5.1. Ethyl 5-(2'-chloro-5'-nitrophenyl)-2-methyl-2,4-pentadienoate (Horner-Emmons reaction)

A solution of 5.3 g of diethyl 3-methyl-3-ethoxycarbonyl-2-propene-1-phosphonate in 10 ml of dimethylformamide (DMF) is added dropwise at 0°-10° C. to a suspension of 0.65 g of 80 percent strength NaH in 30 ml of absolute DMF.

After the mixture has been stirred for two hours at 40° C., evolution of hydrogen is complete; a solution of 3.7 g of 2-chloro-5-nitrobenzaldehyde in 10 ml of DMF is then added dropwise, and stirring is continued for 5 hours at 60° C. Thereafter, 5 ml of methanol are added dropwise, 20 ml of concentrated HCl are introduced and the mixture is extracted with 3 times 100 ml of diethyl ether and washed once with water. Evaporation and chromatography over silica gel with toluene gives 3.8 g (67% of theory) of a solid of melting point 80°-82° C. and of the following structure:

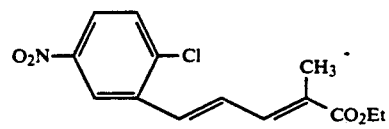

5.2 Reduction of the nitro group The nitro compound obtained according to 5.1 was reduced with iron in ethanol/glacial acetic acid. A yellowish oil is obtained in 96% yield and is converted to the active ingredient without further purification.

5.3 1.35 g of tetrahydrophthalic anhydride and 2.35 g of the aniline derivative obtained according to 5.2 in 25 ml of glacial acetic acid are reacted in the manner described. Working up gives 2.1 g (59% of theory) of the active ingredient of melting point 123°-125° C., which is listed in Table 4 as compound 4-3.

EXAMPLE 6

Desired compound

2-{4-Chloro-3-[(4'-methoxycarbonyl-2',4'-dimethyl-1', 3'-butadienylphenyl]}-4,5,6,7-tetrahydro-2H-isoindole-1,3-dione (active ingredient 4-4 in Table 4)

6.1. 5-(2'-Chloro-5'-nitrophenyl)-2,4-dimethyl-2,4-pentadienoic acid (Perkin condensation) 22.6 g of 2-chloro-5-nitro-α-methylcinnamaldehyde and 9.6 g of sodium propionate are added to 16.3 g of propionic anhydride and the mixture is stirred for 22 hours at 140° C. After cooling, the reaction mixture is poured into 100 ml of water, brought to pH 10 (NaOH) and extracted with ethyl acetate. After the aqueous phase has been acidified with concentrated HCl, the precipitate which has separated out is filtered off with suction, washed with water and dried. 18 g (64% of theory) of a yellow solid of melting point 180°-182° C. and of the following structure are obtained:

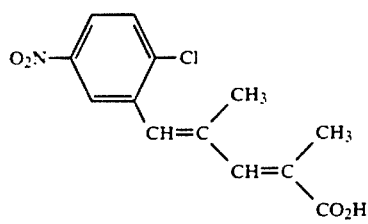

6.2. Methyl 5-(2'-chloro-5'-nitrophenyl)-2,4-dimethyl-2,4-pentadienoate

The acid is esterified with methanol/HCl. The ester of melting point 88°-90° C. is obtained in 78% yield.

6.3. Methyl 5-(2'-chloro-5'-aminophenyl)-2,4-dimethyl-2,4-pentadienoate

The nitro compound is reduced with iron in methanol/glacial acetic acid. 12.3 g (95%) of a yellowish oil is obtained and is used without further purification.

6.4. 2-{4-Chloro-3-[(4'-methoxycarbonyl-2',4'-dimethyl-1',3'-butadienyl)-phenyl]}-4,5,6,7-tetrahydro-2H-isoindole-1,3-dione 12.3 g of the aniline derivative obtained according to 6.3 and 7 g of 2,3-tetramethylenemaleic anhydride in 70 ml of glacial acetic acid are stirred for 2 hours at 40° C. and then heated at the boil for two hours. After the solvent has been separated off in a rotary evaporator, the residue is chromatographed over silica gel with 9:1 n-hexane/acetone and then recrystallized once from methanol. 12.5 g (68% of theory) of a colorless solid of melting point 105°-107° C. are obtained (compound 4-4 in Table 4).

The other compounds listed in Table 4 can be obtained in a similar manner.

EXAMPLE 7

Desired compound

2-{4-Chloro-3-[(4',4'-bis-methoxycarbonyl-1'-butenyl)-phenyl]}-4,5,6,7-tetrahydro-2H-isoindole-1,3-dione (active ingredient 5-1 in Table 5)

7.1. Dimethyl 2-chloro-5-nitrocinnamylidenemalonate 2 ml of piperidine is added to a mixture of 21.7 g of chloro-5-nitrocinnamaldehyde and 26.4 g of dimethyl malonate in 20 ml of DMF and the mixture is heated at 60° C. for 12 hours. Thereafter, all low boilers are stripped off under 0.1 bar and at a bath temperature of 50° C. in a rotary evaporator, the residue is poured into water, and the precipitated solid is stirred with methanol. Filtration under suction and drying under reduced pressure at 50° C. give 15.6 g (48% of theory) of a yellow solid of melting point 167°-168° C.

7.2. Dimethyl 2-chloro-5-aminocinnamylmalonate 50 ml of a freshly prepared saturated solution of Cu(II) acetate in methanol are added to a solution of 4.8 g of the nitro compound obtained according to 7.1 in 100 ml of dioxane. Thereafter, 2 g of NaBH₄ are added a little at a time and the mixture is stirred for 4 hours at 35° C. 300 ml of diethyl ether are then added and the mixture is extracted with NaHCO₃ solution. The aqueous phase is discarded and the ether phase is dried and evaporated down to give 4.18 g (95%) of an oil which is of the following structure:

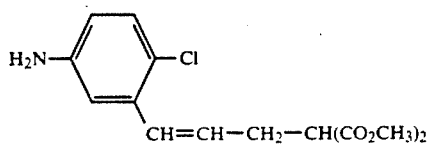

7.3. Tetrahydroisoindole-1,3-dione derivative 2.1 g of 2,3-tetramethylenemaleic anhydride and 4.1 g of the oil obtained according to 7.2 in 25 ml of acetic acid are stirred for 1 hour at 40° C. and then heated for a further hour at 110° C. The solvent is stripped off and the residue is then chromatographed over silica gel with n-hexane to give 3.5 g (58%) of an oil ($n^{24}$=1.5538) of the following structure:

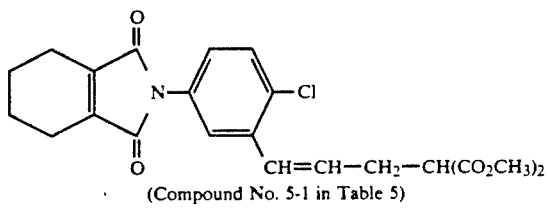

(Compound No. 5-1 in Table 5)

EXAMPLE 8

Desired compound

2-{4-Chloro-3-[(4',4'-bis-methoxycarbonyl-2'-methyl-1'-butenyl)-phenyl]}-4,5,6,7-tetrahydro-2H-isoindole-1,3-dione (active ingredients 5-2 in Table 5)

8.1. 2-Chloro-5-nitro-α-methylcinnmaldehyde

A solution of 2.4 g of NaOH in 20 ml of water is poured into a suspension of 111 g of 2-chloro-5-nitrobenzaldehyde in 500 ml of methanol and the mixture is cooled to 10° C. 42 g of propionaldehyde are then added dropwise. A clear solution is formed, from which a precipitate begins to separate out in the course of 1 hour. Stirring is carried out for 16 hours at 20°-25° C., after which the pH is brought to 5 with acetic acid, the solid is filtered off under suction and the filtrate is evaporated down. The residue and the solid are combined and dissolved in methylene chloride, and the solution is washed with water, dried and evaporated down. The crude product is stirred thoroughly with 1:1 petroleum ether/ether, filtered off under suction and dried. Yield: 109 g (81%); mp. 102°-104° C., 8.2. Dimethyl 2-chloro-5-nitro-α-methylcinnamylidenemalonate 22.6 g of the aldehyde obtained according to 8.1 are added to a solution of 26.4 g of dimethyl malonate in 20 ml of tetrahydrofuran (THF) and finally a solution of 2 ml of piperidine in 10 ml of THF is added dropwise. The mixture is then heated at 60° C. for 4 hours. After the mixture has cooled, the solvent is stripped off under reduced pressure and the residue is stirred with methanol, filtered off under suction and dried under reduced pressure. A yellow solid of melting point 100°-102° C. is obtained. The yield is 19.3 g (57%).

8.3. Dimethyl 2-chloro-5-amino-α-methylcinnamylmalonate

The nitro ester obtained in 8.2 is reduced with $NaBH_4$ in the presence of copper acetate in methanol in the manner described in Example 7.2. 1.4 g (63%) of the desired product are obtained in the form of an oil from 2.4 g of 8.2 by this procedure. The structure is as follows:

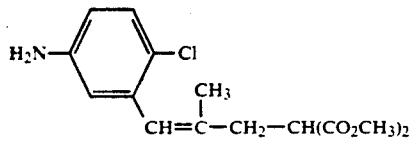

8.4. Tetrahydroisoindole-1,3-dione derivative

The aniline derivative obtained in 8.3 is reacted with 2,3-tetramethylenemaleic anhydride in glacial acetic acid using the procedure in Example 7.3. 1.26 g (63%) of the active ingredient of melting point 84°-86° C., whose structure is shown in Table 5 for compound 5-2, are obtained from 1.4 g of aniline derivative by this procedure. The other compounds in Table 5 can also be obtained in a similar manner.

TABLE 1

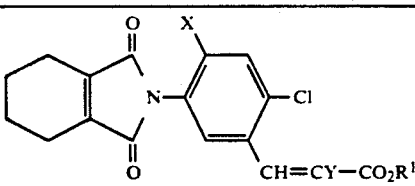

| No. | X | Y | $R^1$ | Physical constant |
|---|---|---|---|---|
| 1-1 | F | Br | $CH_3$ | mp. 121-123° C. |
| 1-2 | F | Br | $C_2H_5$ | mp. 105-110° C. |
| 1-3 | F | Cl | $CH_3$ | |
| 1-4 | F | Cl | $C_2H_5$ | |
| 1-5 | F | Br | $n-C_3H_7$ | |
| 1-6 | F | Br | $n-C_4H_9$ | mp. 55-60° C. |
| 1-7 | F | Br | $n-C_5H_{11}$ | |
| 1-8 | F | Br | $n-C_6H_{13}$ | oil |
| 1-9 | F | Br | $cyclo-C_5H_9$ | |
| 1-10 | F | Br | $cyclo-C_6H_{11}$ | |
| 1-11 | F | Cl | $(CH_2)_2-OCH_3$ | |
| 1-12 | F | Cl | $(CH_2)_2-S-CH_3$ | |

TABLE 2

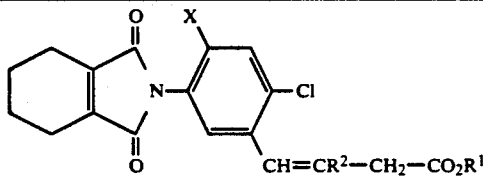

| No. | X | $R^2$ | $R^1$ | Physical constant |
|---|---|---|---|---|
| 2-1 | H | H | $CH_3$ | |

TABLE 2-continued

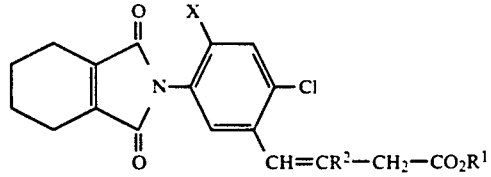

| No. | X | $R^2$ | $R^1$ | Physical constant |
|---|---|---|---|---|
| 2-2 | H | $CH_3$ | $CH_3$ | $n_D^{24}$ = 1.5579 |
| 2-3 | H | $CH_3$ | $C_2H_5$ | |
| 2-4 | H | $CH_3$ | $n-C_4H_9$ | |
| 2-5 | H | $CH_3$ | $-(CH_2)_2OCH_3$ | |
| 2-6 | H | $CH_3$ | $-(CH_2)_2-S-CH_3$ | |
| 2-7 | F | H | $CH_3$ | |
| 2-8 | H | $C_2H_5$ | $CH_3$ | |
| 2-9 | F | $C_2H_5$ | $CH_3$ | |
| 2-10 | H | $C_2H_5$ | $C_2H_5$ | |
| 2-11 | H | $C_2H_5$ | $n-C_4H_9$ | |

TABLE 3

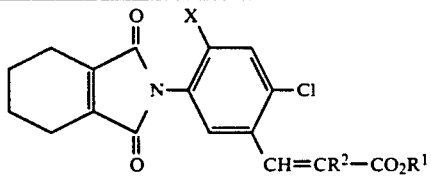

| No. | X | $R^2$ | $R^1$ | Physical constant |
|---|---|---|---|---|
| 3-1 | F | $C_2H_5$ | $CH_3$ | |
| 3-2 | F | $C_2H_5$ | $C_2H_5$ | |
| 3-3 | F | $i-C_3H_7$ | $CH_3$ | |
| 3-4 | F | $n-C_3H_7$ | $CH_3$ | |
| 3-5 | F | $n-C_4H_9$ | $CH_3$ | |

TABLE 4

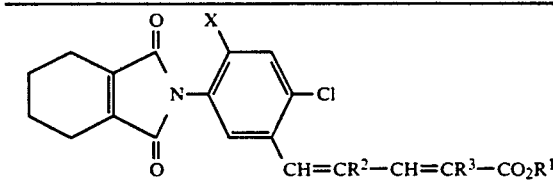

| No. | X | $R^2$ | $R^3$ | $R^1$ | Physical constant |
|---|---|---|---|---|---|
| 4-1 | H | H | H | $CH_3$ | mp. 127-130° C. |
| 4-2 | H | $CH_3$ | H | $CH_3$ | mp. 160-162° C. |
| 4-3 | H | H | $CH_3$ | $C_2H_5$ | mp. 123-125° C. |
| 4-4 | H | $CH_3$ | $CH_3$ | $CH_3$ | mp. 105-107° C. |
| 4-5 | F | H | H | $C_2H_5$ | |
| 4-6 | F | H | H | $n-C_3H_7$ | |
| 4-7 | F | H | H | $n-C_4H_9$ | |
| 4-8 | H | $C_2H_5$ | H | $CH_3$ | |
| 4-9 | H | $CH_3$ | H | $C_2H_5$ | |
| 4-10 | H | $CH_3$ | H | $n-C_4H_9$ | |
| 4-11 | H | $CH_3$ | H | $-(CH_2)_2-OCH_3$ | |
| 4-12 | H | $CH_3$ | H | $-(CH_2)_2-S-CH_3$ | |

TABLE 5

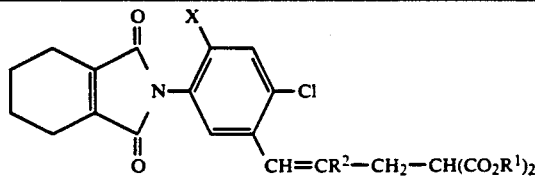

| No. | X | $R^2$ | $R^1$ | Physical constant |
|---|---|---|---|---|
| 5-1 | H | H | $CH_3$ | $n_D^{24}$ = 1.5538 |

TABLE 5-continued

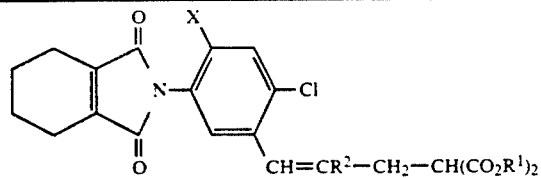

CH=CR²—CH₂—CH(CO₂R¹)₂

| No. | X | R² | R¹ | Physical constant |
|---|---|---|---|---|
| 5-2 | H | CH₃ | CH₃ | mp. 84-86° C. |
| 5-3 | H | C₂H₅ | CH₃ | |
| 5-4 | H | H | C₂H₅ | |
| 5-5 | H | H | n-C₃H₇ | |
| 5-6 | H | H | n-C₄H₉ | |
| 5-7 | H | CH₃ | C₂H₅ | |
| 5-8 | H | CH₃ | n-C₃H₇ | |
| 5-9 | H | CH₃ | n-C₄H₉ | |
| 5-10 | H | CH₃ | —(CH₂)₂OCH₃ | |
| 5-11 | H | CH₃ | —(CH₂)₂OC₂H₅ | |
| 5-12 | H | CH₃ | —(CH₂)₂O—C₄H₉ | |

The compounds according to the invention may be applied either pre- or postemergence. If certain crop plants tolerate the active ingredients less well, application techniques may be employed in which the herbicidal agents are sprayed from suitable equipment in such a way that the leaves of sensitive crop plants are if possible not touched, and the active ingredients reach the soil, or the leaves of the unwanted plants growing below them (post-directed, lay-by treatment).

The amount of active ingredient applied depends on the objective to be achieved, the time of the year, the plants to be combated and their growth stage, and is from 0.005 to 3.0, and preferably from 0.015 to 0.5, kg/ha.

The herbicidal action of the isoindoledione derivatives of the formula I on the growth of test plants is demonstrated in greenhouse experiments.

The vessels employed were plastic flowerpots having a volume of 300 cm³, and which were filled with soil containing about 3.0% humus. The seeds of the test plants were sown separately, according to species.

For the postemergence treatment, the test plants were grown to a height of from 3 to 15 cm, depending on growth shape, before they were treated with suspensions or emulsions of the active ingredients in water as vehicle, sprayed through finely distributing nozzles. Either plants which had been sown in the vessels and grown there were used, or the plants were first grown as seedlings. The application rates for postemergence treatment were 0.015, 0.125 and 0.5 kg of active ingredient per hectare. No covers were placed on the vessels during this treatment.

The pots were set up in the greenhouse-heat-loving species at from 20° to 36° C., and species from moderate climates at from 10° to 20° C. The experiments were run for from 2 to 4 weeks, during which time the plants were tended and their reactions to the various treatments assessed. The scale used for assessment was 0 to 100, 100 denoting non-emergence or complete destruction of at least the visible plant parts.

The plants used in the greenhouse experiments were:

| Latin name | Common name |
|---|---|
| Amaranthus spp. | pigweed |
| Arachis hypogaea | peanuts (groundnuts) |
| Cassia tora | sicklepod |
| Centaurea cyanus | cornflower |
| Chrysanthemum spp. | marigold |
| Galium aparine | catchweed bedstraw |
| Ipomoea spp. | morningglory |
| Lamium amplexicaule | henbit |
| Mercurialis annua | annual mercury |
| Oryza sativa | rice |
| Sesbania exaltata | hemp sesbania (coffeeweed) |
| Solanum nigrum | black nightshade |
| Triticum aestivum | wheat |
| Veronica spp. | speedwell |
| Viola spp. | violet |
| Zea mays | Indian corn |

Compounds nos. 4-1, 4-2, 4-4 and 1-1 have, when applied postemergence at a rate of 0.5 kg/ha, a strong herbicidal action on unwanted broadleaved plants.

Compounds nos. 5-2, 5-1 and 2-2 have a herbicidal action when applied postemergence at a rate of 0.125 kg/ha.

Compound no. 4-2 has, when applied postemergence at a rate of 0.125 kg/ha in wheat, a selective action on broadleaved weeds, while only initial and slight temporary damage was caused to the wheat plants.

Compound no. 4-1 selectively combats unwanted plants when applied postemergence at a rate of 0.125 kg/ha to groundnuts, the latter only suffering brief damage which disappears later.

Unwanted broadleaved plants in wheat, rice and Indian corn are combated with 0.015 kg/ha of compound no. 1-1. If the crop plants suffer any damage at all, it is only temporary and to the foliage.

In view of the wide variety of application methods available, the compounds according to the invention, or agents containing them, may be used in a further large number of crops for combating unwanted plants. Examples are given below:

| Botanical name | Common name |
|---|---|
| Allium cepa | onions |
| Ananas comosus | pineapples |
| Arachis hypogaea | peanuts (groundnuts) |
| Asparagus officinalis | asparagus |
| Avena sativa | oats |
| Beta vulgaris spp. altissima | sugarbeets |
| Beta vulgaris spp. rapa | fodder beets |
| Beta vulgaris spp. esculenta | table beets, red beets |
| Brassica napus var. napus | rapeseed |
| Brassica napus var. napobrassica | swedes |
| Brassica napus var. rapa | turnips |
| Brassica rapa var. silvestris | |
| Camellia sinensis | tea plants |
| Carthamus tinctorius | safflower |
| Carya illinoinensis | pecan trees |
| Citrus limon | lemons |
| Citrus maxima | grapefruits |
| Citrus reticulata | mandarins |
| Citrus sinensis | orange trees |
| Coffea arabica (Coffea canephora, Coffea liberica) | coffee plants |
| Cucumis melo | melons |
| Cucumis sativus | cucumbers |
| Cynodon dactylon | Bermudagrass |
| Daucus carota | carrots |
| Elais guineensis | oil palms |
| Fragaria vesca | strawberries |
| Glycine max | soybeans |
| Gossypium hirsutum (Gossypium arboreum, Gossypium herbaceum, Gossypium vitifolium) | cotton |
| Helianthus annuus | sunflowers |

| Botanical name | Common name |
| --- | --- |
| Helianthus tuberosus | Jerusalem artichoke |
| Hevea brasiliensis | rubber plants |
| Hordeum vulgare | barley |
| Humulus lupulus | hops |
| Ipomoea batatas | sweet potatoes |
| Juglans regia | walnut trees |
| Lactuca sativa | lettuce |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicotiana tabacum (N. rustica) | tobacco |
| Olea europaea | olive trees |
| Oryza sativa | rice |
| Phaseolus lunatus | limabeans |
| Phaseolus mungo | mungbeans |
| Phaseolus vulgaris | snapbeans, green beans, dry beans |
| Pennisetum glaucum | pearl millet |
| Petroselinum crispum spp. tuberosum | parsley |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Secale cereale | rye |
| Sesamum indicum | sesame |
| Solanum tuberosum | Irish potatoes |
| Sorghum bicolor (s. vulgare) | sorghum |
| Sorghum dochna | sorgo |
| Spinacia oleracea | spinach |
| Theobroma cacao | cacao plants |
| Trifolium pratense | red clover |
| Triticum aestivum | wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |
| Zea mays | Indian corn, sweet corn, maize |

To increase the spectrum of action and to achieve synergistic effects, the tetrahydroisoindolediones of the formula I may be mixed and applied together with numerous representatives of other herbicidal or growth-regulating active ingredient groups. Examples of suitable components are diazines, 4H-3,1-benzoxazine derivatives, benzothiadiazinones, 2,6-di-nitroanilines, N-phenylcarbamates, thiolcarbamates, halocarboxylic acids, triazines, amides, ureas, diphenyl ethers, triazinones, uracils, benzofuran derivatives, quinolinecarboxylic acids, phenoxypropionic acid derivatives, cyclohexenones, etc.

It may also be useful to apply the tetrahydroisoindolediones of the formula I, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

We claim:

1. Phenylalkenylcarboxylic acid and esters thereof of the formula I

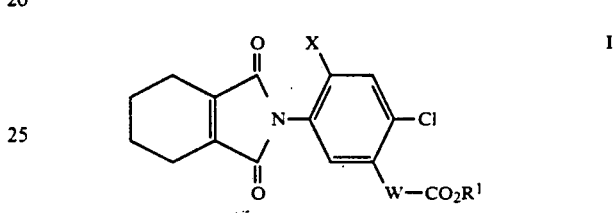

where X is hydrogen or fluorine, $R^1$ is hydrogen, $C_1$-$C_6$-alkyl, $C_5$- or $C_6$-cycloalkyl, ($C_1$-$C_4$-alkoxy)-$C_2$-$C_4$-alkyl or ($C_1$-$C_4$-alkylthio)-$C_2$-$C_4$-alkyl; W is a divalent radical selected from the group consisting of $-CH=CY-$; $-CH=CR^2-CH_2-$; $-CH=CR^2-CH=CR^3-$ or

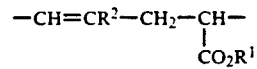

where Y is chlorine or bromine and $R^2$ and $R^3$ are each hydrogen or $C_1$-$C_4$-alkyl, with the proviso that $R^1$ is not $CH_3$ or $CH_2-CH_3$ when X is fluorine, and W is $CH=C-Br$.

2. A herbicidal composition which comprises an effective amount of a compound of the formula I as defined in claim 1 and conventional formulating agents and/or diluents.

3. A process for combating the growth of unwanted plants, wherein an effective amount of a compound I as defined in claim 1 is allowed to act on their habitat.

* * * * *

UNITED STATES PATENT AND TRADEMARK OFFICE
CERTIFICATE OF CORRECTION

PATENT NO. : 5,123,955

DATED : June 23, 1992

INVENTOR(S) : Peter PLATH, Karl EICKEN, Norbert GOETZ, Joachim WILD, Norbert MEYER, Bruno WUERZER It is certified that error appears in the above-identified patent and that said Letters Patent is hereby corrected as shown below:

On the title page, Item [73] Assignee:
    Under assignee, insert "BASF Aktiengesellschaft,
                                    Ludwigshafen, Fed. Rep. Of
                                    Germany "

On the title page, Item [56]:
    Under Agent, Attorney or Firm, insert " Keil & Weinkauf"

Signed and Sealed this

Twenty-sixth Day of October, 1993

Attest:

BRUCE LEHMAN

*Attesting Officer*        *Commissioner of Patents and Trademarks*